US012599966B2

(12) United States Patent
English et al.

(10) Patent No.: US 12,599,966 B2
(45) Date of Patent: Apr. 14, 2026

(54) ADDITIVE MANNUFACTURING OF A MEDICAL DEVICE

(71) Applicant: BOSTON SCIENTIFIC SCIMED, INC., Maple Grove, MN (US)

(72) Inventors: James Michael English, County Tipperary (IE); Robert Hannon, County Tipperary (IE); Mark David Mirigian, County Kilkenny (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1160 days.

(21) Appl. No.: 17/534,928

(22) Filed: Nov. 24, 2021

(65) Prior Publication Data

US 2022/0161327 A1 May 26, 2022

Related U.S. Application Data

(60) Provisional application No. 63/117,778, filed on Nov. 24, 2020.

(51) Int. Cl.
*B22F 10/28* (2021.01)
*A61F 2/91* (2013.01)
(Continued)

(52) U.S. Cl.
CPC ................ *B22F 10/28* (2021.01); *A61F 2/91* (2013.01); *B33Y 10/00* (2014.12); *B33Y 80/00* (2014.12);
(Continued)

(58) Field of Classification Search
CPC .................. B22F 10/28; B22F 2301/15; B22F 2301/205; B22F 2999/00; B22F 10/32;
(Continued)

(56) References Cited

U.S. PATENT DOCUMENTS 6,465,758 B1 10/2002 Ham
6,517,888 B1 2/2003 Weber
(Continued)

FOREIGN PATENT DOCUMENTS

EP        1244389 A2    10/2002
EP        3797903 A1 *   3/2021    .............. B22F 10/00
WO    2020163915 A1     8/2020

OTHER PUBLICATIONS

Boley et al., "Calculation of laser absorption by metal powders in additive manufacturing," Applied Optics, 54(9): 2477-2482, Mar. 20, 2015.
(Continued)

*Primary Examiner* — John A Hevey
(74) *Attorney, Agent, or Firm* — Seager, Tufte & Wickhem, LLP

(57) ABSTRACT

An example method for manufacturing an object is disclosed. The example method includes determining the material composition of a base material, wherein determining the material composition of the base material includes determining the relative percentage of a first metal and the relative percentage of a second metal forming the base material. The method further includes selecting a common laser processing wavelength to be used in processing the base material. The method further includes processing the base material with a laser to form a processed material, the laser emits a laser beam matching the common laser processing wavelength during the processing of the base material and the material composition of the processed material is substantially similar to the material composition of the base material.

17 Claims, 3 Drawing Sheets

100

Raw Material — 102

↓

Determine % composition of raw material — 104

↓

Select wavelength for material processing — 106

↓

Process material using selected wavelength — 108

↓

Analyze composition of processed material — 110

(51) Int. Cl.
  *B33Y 10/00* (2015.01)
  *B33Y 80/00* (2015.01)
(52) U.S. Cl.
  CPC . *A61F 2210/0076* (2013.01); *A61F 2240/002* (2013.01); *B22F 2301/15* (2013.01); *B22F 2301/205* (2013.01)
(58) Field of Classification Search
  CPC .... B22F 10/36; A61F 2/91; A61F 2210/0076; A61F 2240/002; A61F 2/90; A61F 2240/001; B33Y 10/00; B33Y 80/00; B33Y 70/00; Y02P 10/25; C22C 19/03; C22C 1/0433; C22C 1/0458
  See application file for complete search history.

(56) References Cited

U.S. PATENT DOCUMENTS

| | | | |
|---|---|---|---|
| 6,586,134 B2 | 7/2003 | Skoumpris | |
| 8,279,903 B2 | 10/2012 | Shah et al. | |
| 8,293,261 B2 | 10/2012 | Nagura | |
| 8,436,251 B2 | 5/2013 | Boyd | |
| 8,585,753 B2 | 11/2013 | Scanlon et al. | |
| 8,728,149 B2 | 5/2014 | Atladottir et al. | |
| 9,393,134 B2 | 7/2016 | Harrington et al. | |
| 9,510,961 B2 | 12/2016 | Kim | |
| 9,597,518 B2 | 3/2017 | Deininger et al. | |
| 9,844,612 B2 | 12/2017 | Wang et al. | |
| 10,124,437 B2 | 11/2018 | Maeso et al. | |
| 10,213,611 B2 | 2/2019 | Kim et al. | |
| 10,238,512 B2 | 3/2019 | Frid | |
| 10,426,645 B2 | 10/2019 | Kim | |
| 10,525,552 B2 | 1/2020 | Harrington et al. | |
| 11,014,162 B2 | 5/2021 | Hofmann | |
| 2006/0108064 A1 | 5/2006 | Mori | |
| 2016/0067827 A1* | 3/2016 | Zediker | B23K 26/144 219/76.12 |
| 2018/0078738 A1 | 3/2018 | Yazdanpanah et al. | |
| 2020/0016657 A1 | 1/2020 | Hart et al. | |
| 2022/0126368 A1* | 4/2022 | Lathabai | B22F 10/28 |

OTHER PUBLICATIONS

Mwangi et al., "Nitinol manufacturing and micromachining: A review of processes and their suitability in processing medical-grade nitinol," Journal of Manufacturing Processes, 38: 355-369, 2019.
International Search Report and Written Opinion dated Mar. 25, 2022 for International Application No. PCT/US2021/060746.

\* cited by examiner

ADDITIVE MANNUFACTURING OF A MEDICAL DEVICE

CROSS REFERENCE TO RELATED APPLICATIONS

The present application claims the benefit of and priority to U.S. Prov. Pat. App. No. 63/117,778, filed Nov. 24, 2020 and titled ADDITIVE MANUFACTURING OF A MEDICAL DEVICE, the disclosure of which is incorporated herein by reference.

TECHNICAL FIELD

The present disclosure pertains to medical devices, and methods for manufacturing medical devices. More particularly, the present disclosure pertains to using predetermined laser wavelengths to control the material chemistry of medical devices processed via additive manufacturing.

BACKGROUND

Additive manufacturing (AM) is an approach to component production that may enable the creation of improved medical devices while reducing manufacturing costs and timelines. Additive manufacturing is a manufacturing process that uses data computer-aided-design (CAD) software and/or 3D object scanners to direct hardware to deposit material (e.g., metallic powder), layer upon layer, in precise geometric shapes.

Traditional manufacturing processes may create medical devices via the removal of material from a previously formed structure via milling, machining, etching, or other means. For example, traditional manufacturing of medical stents may be accomplished by laser micro-cutting a pre-formed metal tube. The laser cutting process may remove selected material from the preformed tube, thereby leaving a tubular member having a desired stent geometry. However, it may be possible to improve upon traditional manufacturing techniques to achieve improved medical devices at a reduced cost. For example, 3D additive manufacturing (e.g., "3D printing", "rapid prototyping") techniques may be utilized to manufacture a variety of medical devices at a reduced cost, while preserving superior performance capabilities of the medical devices.

As discussed above, additive manufacturing processing may deposit material (e.g., metallic powder), layer upon layer, to form finished medical devices. Further, depositing the material may be accomplished via a laser which sinters the metallic powder together, prior to the laser depositing another layer of powder atop the previously sintered metallic layer. This process may repeat itself until the medical device is completely formed. Additive manufacturing processes which optimize the laser sintering process are disclosed herein.

BRIEF SUMMARY

This disclosure provides design, material, manufacturing method, and use alternatives for medical devices. An example method for manufacturing a medical device includes determining the material composition of a base material, wherein determining the material composition of the base material includes determining the relative percentage of a first metal and the relative percentage of a second metal forming the base material. The method further includes selecting a common laser processing wavelength to be used in processing the base material. The method further includes processing the base material with a laser to form a processed material, the laser emits a laser beam matching the common laser processing wavelength during the processing of the base material and the material composition of the processed material is substantially similar to the material composition of the base material.

Alternatively or additionally, wherein selecting the common laser processing wavelength to be used in the processing of the base material further includes analyzing an absorption wavelength spectrum for the first metal and an absorption wavelength spectrum for the second metal.

Alternatively or additionally, wherein selecting the common laser processing wavelength to be used in the processing of the base material further includes comparing the absorption wavelength spectrum for the first metal and an absorption wavelength spectrum for the second metal to determine a common laser wavelength which does not excite a plurality of atoms of the first metal at a substantially higher rate than a plurality of atoms of the second metal.

Alternatively or additionally, wherein the first metal is nickel and the second metal is titanium.

Alternatively or additionally, wherein the common laser wavelength is between 424 nm and 425 nm.

Alternatively or additionally, wherein the relative percentage of the first metal and the relative percentage of a second metal in the processed material differ by less than 0.15%.

Alternatively or additionally, wherein processing the base material with a laser to form the processed material includes laser sintering.

Alternatively or additionally, wherein processing the base material with a laser to form the processed material includes additive manufacturing processing.

Alternatively or additionally, wherein the method further includes processing the base material at a pressure between 2 ATM and 10 ATM, and wherein processing the base material at a pressure between 2 ATM and 10 ATM is designed to increase the vaporization temperature of the first metal and the second metal.

Alternatively or additionally, wherein the method further includes processing the base material at a pressure between 1.5 ATM and 4 ATM, and wherein processing the base material at a pressure between 1.5 ATM and 4 ATM is designed to limit the presence of one or more voids in the processed material.

Another method of manufacturing a metallic stent includes determining the material composition of a metallic powder, wherein determining the material composition of the metallic powder includes determining the relative percentage of a first metal and the relative percentage of a second metal forming the metallic powder. The method further includes determining a first wavelength spectrum for the first metal. The method further includes determining a second wavelength spectrum for the second metal. The method further includes comparing the first wavelength spectrum to the second wavelength spectrum to determine a common laser processing wavelength. The method further includes processing the metallic powder with a laser to form the stent, wherein the laser emits a laser beam matching the common laser processing wavelength during the processing of the metallic powder, and wherein the material composition of the stent is substantially similar to the material composition of the metallic powder.

Alternatively or additionally, wherein processing the metallic powder with a laser at a common laser processing wavelength to form the stent does not excite a plurality of atoms of the first metal at a substantially higher rate than a plurality of atoms of the second metal.

Alternatively or additionally, wherein the common laser wavelength is between 424 and 425 nm.

Alternatively or additionally, wherein the relative percentage of the first metal and the relative percentage of a second metal in the stent differ by less than 0.15%.

Alternatively or additionally, wherein processing the metallic powder with a laser to form the processed material includes laser sintering.

Alternatively or additionally, wherein processing the metallic powder with a laser to form the processed material includes additive manufacturing processing.

Alternatively or additionally, wherein the method further includes processing the metallic powder at a pressure between 2 ATM and 10 ATM, and wherein processing the base material at a pressure between 2 ATM and 10 ATM is designed to increase the vaporization temperature of the first metal and the second metal.

Alternatively or additionally, wherein the method further includes processing the base material at a pressure between 1.5 ATM and 4 ATM, and wherein processing the base material at a pressure between 1.5 ATM and 4 ATM is designed to limit the presence of one or more voids in the processed material.

An example stent includes a metallic scaffold, the metallic scaffold formed from a metallic alloy, wherein forming the metallic scaffold includes laser sintering a base powder to form the metallic alloy, wherein the base powder is formed from a first metal and a second metal, and wherein laser sintering the base powder includes using a laser to emit a laser wavelength configured to excite a plurality of atoms of the first metal at a substantially equal rate as a plurality of atoms of the second metal.

Alternatively or additionally, wherein the first metal is nickel and the second metal is titanium.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
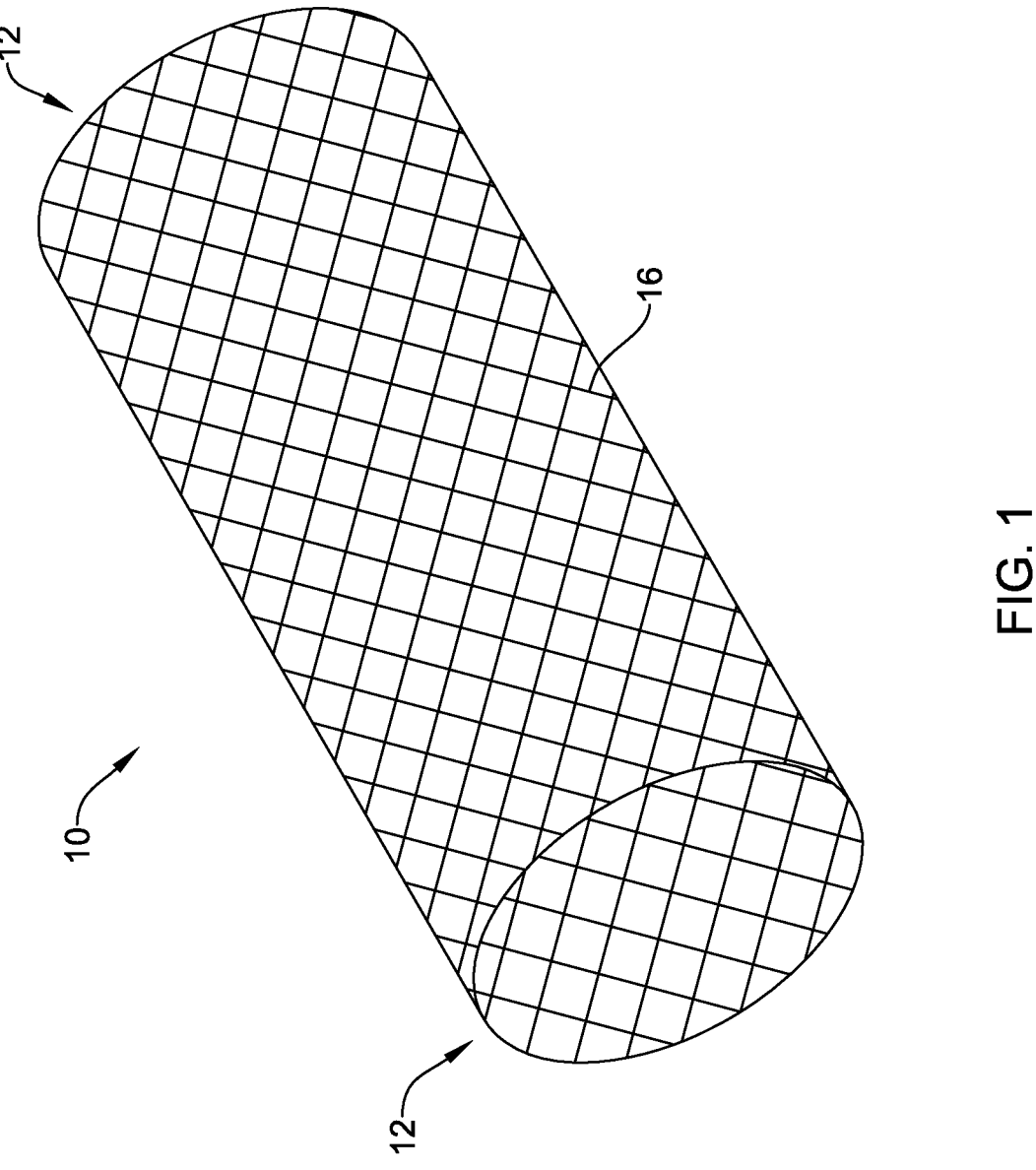
FIG. 1 is an example stent.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Additionally, although the additive material processing techniques described here may be discussed with specific reference to endovascular stents in the particular embodiments described herein, the disclosure may be applicable to a variety of medical devices. For example, the disclosure may be applicable to heart valve replacement devices and components thereof, self-expanding stents, balloon-expandable stents, occlusion devices, cardiovascular filters (e.g., IVC filters), fixed wire devices, guidewires, a variety of catheters (e.g., balloon, stent delivery, etc.), drive shafts for rotational devices such as atherectomy catheters and IVUS catheters, endoscopic devices, is laparoscopic devices, embolic protection devices, sensors, spinal or cranial navigational devices, implantable leads, implantable monitors, active implants, skeletal fixation hardware, cochlear implants and other such devices.

Additionally, while some embodiments may be adapted or configured for use within the vasculature of a patient, other embodiments may be adapted and/or configured for use in other anatomies. It is to be understood that a broad variety of materials, dimensions and structures can be used to construct suitable embodiments, depending on the desired characteristics. The following examples of some embodiments are included by way of example only and are not intended to be limiting. Further, medical devices formed from the additive manufacturing processes described herein may comprise one or more materials that exhibit shape memory behavior, superelastic behavior, or both. These materials can be metal alloys, for example Nitinol®.

In general, certain nickel-titanium (Ni—Ti) alloys can exhibit shape memory or superelastic (or pseudoelastic) behavior, or both. Although Nitinol® is essentially a binary alloy with nickel and titanium, some superelastic and/or shape memory Ni:Ti alloys can contain additional elements, such as cobalt or vanadium. In addition, some other alloys exhibit shape memory or superelastic behavior or, like some Ni:Ti alloys, both shape memory and superelasticity. Some examples of these alloys are: AgCd, AuCd, AuCu, CuAlNi, CuAuZn, CuSn, CuZn, CuZnSi, CuZnSn, CuZnAl, CuZnGa, CuZnXe, CuAlNi, InTl, NiAl, FePt, FePd, FeMn, Fe3Be, Fe3Pt, FeNiTiCo, and MnCu.

Superelasticity and shape memory are two distinct manifestations of a reversible phase transformation. Superelasticity may be defined as a nonlinear recoverable deformation behavior of Ni—Ti shape memory alloys at temperatures above the austenite finish temperature (Af). The nonlinear deformation arises from the stress induced formation of martensite on loading and the spontaneous reversion of this crystal structure to austenite upon unloading. A shape memory alloy may be defined as a metal which, after an apparent plastic deformation in the martensitic phase, undergoes a thermoelastic change in crystal structure when heated through its transformation temperature range, resulting in a recovery of the deformation. The unique crystalline structure of Ni—Ti alloys may result in variable responses to additive manufacturing techniques, as described below.

FIG. 1 illustrates an example stent 10. The stent 10 may include one or more stent strut members 16 which extend from a first end region 12 to a second end region 14. The stent strut members 16 may extend longitudinally along the stent 10. While FIG. 1 shows the stent strut members 16 extending along the entire length of the stent 10, in other examples, the stent strut members 16 may extend only along a part of the stent 10.

In some instances, the stent 10 may be a self-expanding stent or the stent 10 may be a balloon expandable stent. Self-expanding stent examples may include stents having one or more struts 16 combined to form a rigid and/or semi-rigid stent structure. For example, the stent 10 may be a rigid or semi-rigid structure formed from an additive manufacturing process (e.g., 3D laser printing). Openings or interstices through the wall of the stent 10 may be defined between adjacent stent struts 16.

The stent 10 in examples disclosed herein may be constructed from a variety of materials. For example, the stent 10 (e.g., self-expanding or balloon expandable) may be constructed from a metal (e.g., Nitinol® or other metallic alloys including Nitinol®). In other instances, the stent 10 may be constructed from a polymeric material (e.g., PET). In yet other instances, the stent 10 may be constructed from a combination of metallic and polymeric materials. Additionally, the stent 10 may include a bioabsorbable and/or biodegradable material.

During use, the stent 10 may be expanded from an initial, small diameter to a larger diameter such that the stent 10 contacts a wall of a vessel, thereby maintaining the patency of the vessel. The stent struts 16 may provide the stent 10 with flexibility and conformability so that the stent 10 can adapt to the contours of the vessel.

The stent 10 may include (e.g., be formed of) a biocompatible alloy composition that is capable of providing the stent 10 with a complimentary combination of physical properties and mechanical properties that enhances the performance of the stent 10. For example, the alloy composition may include relatively dense elements that enhance the radiopacity of the stent 10. As a result, the stent 10 may be easily detected during X-ray fluoroscopy and CT. The alloy composition may also include elements that have low magnetic susceptibility. As a result, the stent 10 may be compatible with MM techniques.

At the same time, the metallic alloy used to form stent 10 may have mechanical properties that allow it to be manipulated within a stent delivery system and to provide the device with good mechanical performance characteristics. For example, the alloy composition may have a stiffness or elastic modulus to provide the stent 10 with reduced recoil, e.g., when the stent is crimped on a delivery catheter or when the stent is expanded against a vessel wall.

Figure 2:
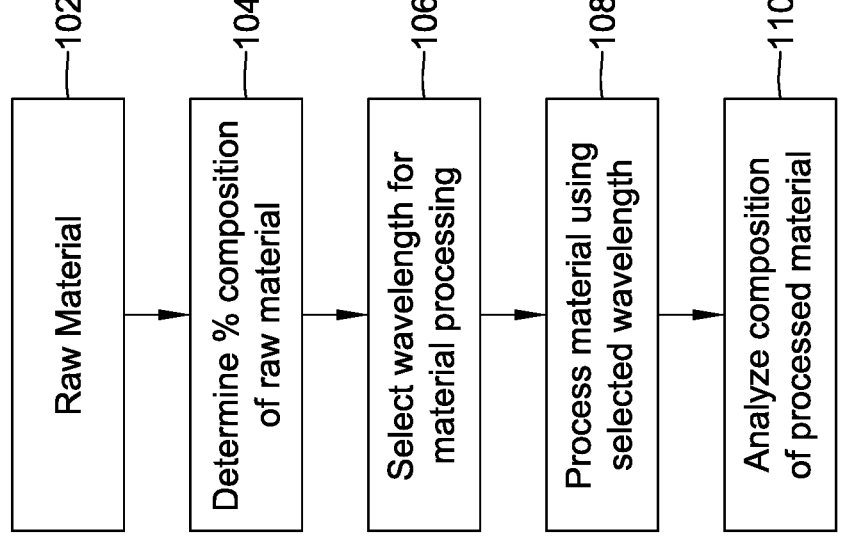
FIG. 2 is a flow diagram of an example additive manufacturing process.

FIG. 2 illustrates an example flow diagram 100 for utilizing additive manufacturing processes to manufacture example medical devices. For example, the flow diagram 100 shown in FIG. 2 may be utilized to manufacture the medical stent 10 illustrated in FIG. 1. However, as discussed above, the example flow diagram 100 shown in FIG. 2 may be utilized to form a variety of medical devices (some of which are disclosed above) and is not limited to the stent 10 shown in FIG. 1.

An example first step in the additive manufacturing process shown in FIG. 2 may include obtaining 102 a raw (stock) material from which a final processed object/component (e.g., a medical device) may be formed. It can be appreciated that the raw material used in the additive manufacturing process 100 may include a raw metallic powder. The raw metallic powder may be formed of two or more metals, and thus, may be commonly referred to as a metallic alloy powder. It can be appreciated that the raw metallic powder may include two or more metals, which may exist in different (relative) proportions within the raw powder. For example, a raw metallic powder used in the additive manufacturing step 102 may include nickel and titanium (e.g., a Ni—Ti alloy powder), whereby both nickel and titanium are present at different relative proportions within the raw metallic powder.

In some additive manufacturing processing, it may be desirable to obtain a raw Ni—Ti alloy powder having a relatively equal percentage of both nickel and titanium. In other words, in some additive manufacturing processing techniques, it may be desirable to begin the manufacturing process with a Ni—Ti alloy powder having approximately 50% nickel and 50% titanium. However, this is not intended to be limiting. It is appreciated that the additive manufacturing techniques utilized herein may be applicable to a variety of different metallic alloys, some of which may include alternative compositions of Ni—Ti alloys.

After selecting a raw metallic powder to be used in the manufacturing process, an example next step may include determining 104 (e.g., confirming) the base elements (e.g., metals) that are present in the metallic powder. In some examples, the relative percentage of each base element (e.g., metal) present in the raw powder may be determined in step 104.

One technique which may be utilized to determine the base elements that are present in the raw material may including performing a chemical composition test on the raw metallic powder. The chemical composition test may determine what base metals and chemicals are present in the raw sample in addition to determining the relative percentage of each base metal and chemical that is present.

As discussed above, the additive manufacturing process may further include using a laser (e.g., using a laser printer or similar device) to sinter the raw metallic powder layer-by-layer via a 3D laser printing process into a finished component (e.g., a finished medical device). Generally, the laser sintering process may include applying a laser beam having a wavelength (which may be expressed in nanometers) and power (which may be expressed in Watts) to a bed of the raw metallic powder. In some instances, the laser beam may be applied to the raw metallic powder inside a pressurized chamber of inert gas. It can be appreciated that the energy applied by the laser may be intense enough to permit the melting of the metallic powder to form a solid metal. This laser process is repeated layer after layer until the finished component is complete, whereby each new layer is subsequently fused to the previous layer.

In some instances, applying energy via the laser beam may excite the atoms of one of the base materials to a greater extent than another of the base materials. For example, applying a laser beam having a particular wavelength and a particular power to a Ni—Ti alloy may excite the nickel atoms at a higher rate than the titanium atoms. This unequal absorption of energy between the nickel atoms and the titanium atoms may result in a higher level of vaporization (e.g., the unequal heating) of the nickel atoms compared to the titanium atoms. Further, it can be appreciated that the unequal rates of vaporization of the nickel atoms versus the titanium atoms may result in the final processed medical device to include a different percentage of nickel atoms than titanium atoms compared to the starting percentage of nickel atoms and titanium atoms in the base metallic powder (e.g., the raw stock powder).

For example, as described above, initially the base metallic powder may include relative percentages of nickel atoms and titanium atoms to be approximately 54% nickel and 46% titanium. However, after processing the metallic powder at a particular wavelength and a particular power, the final processed component (e.g., medical device) may have a relative percentage of nickel atoms and titanium atoms at 51% nickel and 49% titanium, for example.

It can further be appreciated that changing the relative percentages of nickel atoms and titanium atoms during the processing steps may directly influence the performance of the final processed component. For example, the example stent 10 described above may be designed to exhibit a specific Ni—Ti transition temperature corresponding to a 54/46 ratio of nickel atoms to titanium atoms. Accordingly, changing the ratio of nickel atoms and titanium atoms to something other than a 54/46 ratio (for example, a 51/49 ratio of nickel atoms to titanium atoms), may result in the stent 10 having a transition temperature which is different (and, hence, possibly less desirable) for the stent's 10 performance in vivo. Therefore, it may be desirable to minimize the unequal vaporization of nickel atoms versus titanium atoms during the laser processing methodology described herein.

An example method to minimizing the unequal vaporization of nickel atoms versus titanium atoms during the laser processing of a Ni—Ti alloy may include applying the laser energy at a wavelength which does not excite the atoms of one base element (e.g., nickel) at a higher rate than the other base element (e.g., titanium). Step 106 of the additive manufacturing process shown in FIG. 2 illustrates a method step of selecting a wavelength "common" to both base elements (e.g., nickel and titanium) such that applying the laser energy at this common wavelength does not excite the atoms of one base element (e.g., nickel) at a higher rate than the other base element (e.g., titanium).

Identifying a wavelength common to both base elements (e.g., nickel and titanium) such that applying the laser energy at this common wavelength does not excite the atoms of one base element (e.g., nickel) at a higher rate than the other base element (e.g., titanium) may include comparing the emission and absorption spectrum for each base element (e.g., nickel and titanium) to identify common wavelengths at which neither of the targeted base elements (e.g., nickel and titanium) absorb light. Examples of common wavelengths at which neither nickel nor titanium readily absorb light (as determined by comparing the emission and absorption spectrum for nickel and titanium) may include wavelengths about 400-600 nm, or about 495-570 nm, or about 424.68+/−0.05 nm.

In another example methodology, minimizing the unequal vaporization of nickel atoms versus titanium atoms during the laser processing of a Ni—Ti alloy may include applying the laser energy at a wavelength which targets the absorption spectrum of an element having a higher melting temperature as compared to an element having a relatively lower melting temperature. However, when analyzing the absorption spectrum of the element having a higher melting temperature, a wavelength may be chosen which does not interact with the absorption spectrum of the lower melting temperature element. For the example, a wavelength for which one higher melting temperature element (e.g., titanium) readily absorbs light and a relatively lower melting temperature element (e.g., nickel) does not may include a wavelength of 659 nm+/−1.0 nm.

It can be appreciated that after using the emission and absorption spectrum for each base element to identify a wavelength common to each base element (e.g., nickel and titanium), the laser parameters may be adjusted such that the laser emits its laser beam at the predetermined common wavelength when processing the raw metallic powder (as discussed above). It can be further appreciated that processing 108 the raw metallic powder at the predetermined common wavelength will result in even heating of the targeted base metals (e.g., the base materials for which the emission and absorption spectrums were compared). The even heating (and melting) of the base metals in the raw powder during the laser sintering process may be result in a finished component which includes a substantially zero net change in the proportion of base metal atoms (e.g., zero net change in the proportion of nickel atoms versus titanium atoms) between the raw metallic powder and the finished component.

FIG. 2 illustrates that a final step in the additive manufacturing process 100 may include analyzing the finished component to assure a substantially zero net change in the proportion of base metal atoms (e.g., zero net change in the proportion of nickel atoms versus titanium atoms) between the raw metallic powder and the finished component. Having zero net change in the proportion of the respective base metal atoms may assure that the performance characteristics of the finished component (e.g., a medical device such as the stent 10 described above) are preserved from the raw metallic powder to the finished component.

Figure 3:
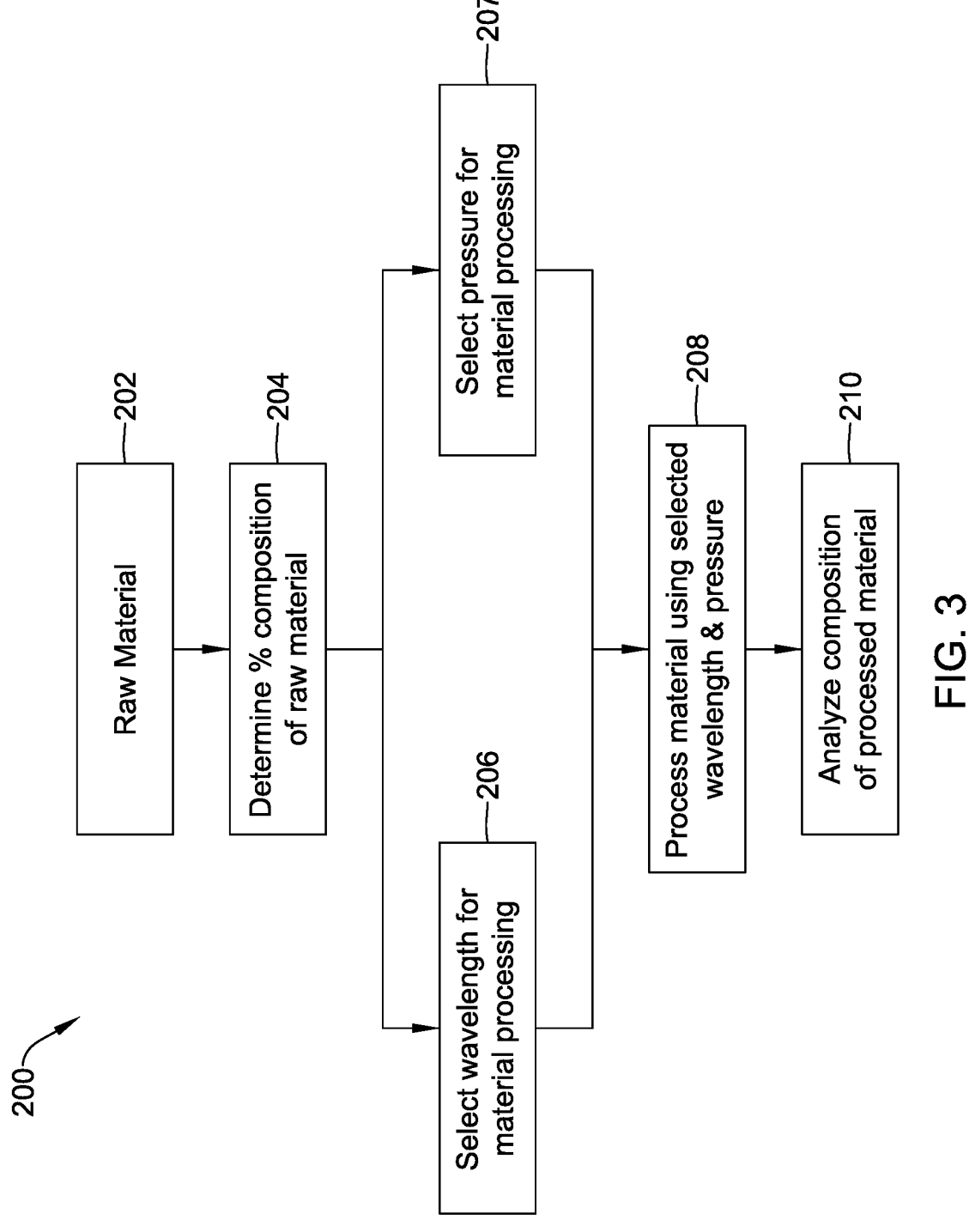
FIG. 3 is a flow diagram of an example additive manufacturing process.

FIG. 3 illustrates another example additive manufacturing process 200. The additive manufacturing process 200 may share several steps with the additive manufacturing process 100 described above. For example, steps illustrated by the boxes 202, 204, 206, 208 and 210 in FIG. 2 may be substantially similar to the disclosure set forth above with respect to the steps 102, 104, 106 and 110, as described above with respect to FIG. 1.

However, FIG. 3 illustrates that, in some examples, the additive manufacturing process 200 may include an additional step 207 which preselects a pressure at which the laser may apply the laser beam (having a preselected common wavelength, as described above) during the processing 208 of the raw metallic powder. It can be appreciated that the laser sintering process (as described above) may be performed inside a pressurized chamber, thereby permitting control of the pressure at which the laser beam may be applied.

It can further be appreciated that pressurizing the laser chamber gas environment during the laser sintering process may increase the vaporization temperatures of each of the base metal elements in the raw metallic powder. Further, the vaporization temperature of each base metal element may increase to a level which is much higher than the melting point of each base element (and also to levels which are much higher than a traditional laser may apply), thereby ensuring that appropriate melting is taking place during the sintering process and that there is no preferential vaporization and, subsequently, no unequal loss of base element atoms during this processing step.

In some examples, the laser chamber gas environment may be pressurized to a range of about 2 ATM to 10 ATM. In yet other examples, the laser chamber gas environment may be pressurized to a range of about 1.5 ATM to 4 ATM, which may be considered a relatively lower pressure as compared with the laser processing at a relatively higher pressure, as previously described. Performing the laser sintering process at a relatively lower pressure (e.g., between 1.5 ATM to 4 ATM), may significantly reduce (or eliminate) voids from forming in the finished component. In other words, performing the laser sintering process at this relatively lower pressure may compress and remove bubbles (e.g., voids), which may otherwise form in the finished product.

It is noted that while the above discussion has primarily focused on characteristics of laser processing Ni—Ti alloys and related alloys thereof, the same analysis may be applied to alloys including any other base metal elements. In other words, the same processing techniques, including comparing emission and absorption spectrums to find common wavelengths, and increasing pressure during the laser sintering process may be applied to alloys having any base metal elements.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A method of manufacturing a medical device, the method comprising:
   determining the material composition of a base material, wherein the base material includes a first percentage of a first metal and a second percentage of a second metal;
   selecting a laser processing wavelength which is common to both the first metal and the second metal;
   processing the base material with a laser to form a first layer of processed material, wherein the laser emits a laser beam matching the laser processing wavelength which is common to both the first metal and the second metal during the processing of the base material;
   disposing additional base material on the first layer of the processed material;
   processing the additional base material disposed on the first layer of the processed material to form a second layer of processed material which is fused with the first layer of processed material, wherein the fused first and second layers of processed material form at least a portion of the medical device;
   wherein processing the base material to form the medical device with the laser processing wavelength which is common to both the first metal and the second metal minimizes an unequal vaporization of the first metal relative to the second metal.

2. The method of claim 1, wherein selecting the laser processing wavelength which is common to both the first metal and the second metal to be used in the processing of the base material further includes analyzing an absorption wavelength spectrum for the first metal and an absorption wavelength spectrum for the second metal.

3. The method of claim 2, wherein selecting the laser processing wavelength which is common to both the first metal and the second metal to be used in the processing of the base material further includes comparing the absorption wavelength spectrum for the first metal and an absorption wavelength spectrum for the second metal to determine the laser processing wavelength which is common to both the first metal and the second metal which minimizes an unequal vaporization of the first metal relative to the second metal.

4. The method of claim 3, wherein the first metal is nickel and the second metal is titanium.

5. The method of claim 4, wherein the laser processing wavelength which is common to both the first metal and the second metal is between 49 nm and 410 nm.

6. The method of claim 1, wherein the relative percentage of the first metal and the relative percentage of a second metal in the processed material differ by less than 0.15%.

7. The method of claim 1, wherein processing the base material with a laser to form the processed material includes laser sintering.

8. The method of claim 1, wherein processing the base material with a laser to form the processed material includes additive manufacturing processing.

9. The method of claim 1, wherein the method further includes processing the base material at a pressure between 2 ATM and 10 ATM, and wherein processing the base material at a pressure between 2 ATM and 10 ATM is designed to increase the vaporization temperature of the first metal and the second metal.

10. The method of claim 1, wherein the method further includes processing the base material at a pressure between 1.5 ATM and 4 ATM, and wherein processing the base material at a pressure between 1.5 ATM and 4 ATM is designed to limit the presence of one or more voids in the processed material.

11. A method of manufacturing a metallic stent, the method comprising:
   determining the material composition of a metallic powder, wherein determining the material composition of the metallic powder includes determining the relative percentage of a first metal and the relative percentage of a second metal forming the metallic powder;
   determining a first wavelength spectrum for the first metal;
   determining a second wavelength spectrum for the second metal;
   comparing the first wavelength spectrum to the second wavelength spectrum to determine a laser processing wavelength which is common to both the first metal and the second metal; and
   processing the metallic powder with a laser to form the stent, wherein the laser emits a laser beam matching the laser processing wavelength which is common to both the first metal and the second metal during the processing of the metallic powder, and wherein processing the metallic powder to form the stent with the laser processing wavelength common to both the first metal and the second metal minimizes an unequal vaporization of the first metal relative to the second metal.

12. The method of claim 11, wherein laser processing wavelength which is common to both the first metal and the second metal is between 49 and 410 nm.

13. The method of claim 12, wherein the relative percentage of the first metal and the relative percentage of a second metal in the stent differ by less than 0.15%.

14. The method of claim 11, wherein processing the metallic powder with a laser to form the processed material includes laser sintering.

15. The method of claim 11, wherein processing the metallic powder with a laser to form the processed material includes additive manufacturing processing.

16. The method of claim 11, wherein the method further includes processing the metallic powder at a pressure between 2 ATM and 10 ATM, and wherein processing the base material at a pressure between 2 ATM and 10 ATM is designed to increase the vaporization temperature of the first metal and the second metal.

17. The method of claim 11, wherein the method further includes processing the base material at a pressure between 1.5 ATM and 4 ATM, and wherein processing the base material at a pressure between 1.5 ATM and 4 ATM is designed to limit the presence of one or more voids in the processed material.

* * * * *